(12) United States Patent
Dawson et al.

(10) Patent No.: US 6,897,033 B2
(45) Date of Patent: May 24, 2005

(54) FUNGAL LIPASE

(75) Inventors: Thomas Larry Dawson, Hamilton, OH (US); Yvonne Marie Deangelis, Cincinnati, OH (US); Kevin Robert Johnstone, Cincinnati, OH (US); Joseph Robert Kaczvinsky, Jr., Cincinnati, OH (US); Charles Winston Saunders, Fairfield, OH (US); Richard Lee Walter, Jr., Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/369,800

(22) Filed: Feb. 19, 2003

(65) Prior Publication Data

US 2003/0158385 A1 Aug. 21, 2003

Related U.S. Application Data

(60) Provisional application No. 60/357,801, filed on Feb. 19, 2002, provisional application No. 60/358,198, filed on Feb. 20, 2002, and provisional application No. 60/361,003, filed on Mar. 1, 2002.

(51) Int. Cl.[7] .............................. C12Q 1/44; C12N 9/20; C07H 21/04
(52) U.S. Cl. .................... 435/19; 435/198; 536/23.2
(58) Field of Search ................... 435/19, 198; 536/23.2

(56) References Cited

U.S. PATENT DOCUMENTS

| | | | |
|---|---|---|---|
| 5,733,473 A | 3/1998 | Johnston et al. | |
| 5,827,718 A | 10/1998 | Ishida et al. | |
| 5,942,431 A | 8/1999 | Yoneda et al. | |
| 6,020,180 A | 2/2000 | Svendsen et al. | |
| 6,093,563 A | 7/2000 | Bennett et al. | |
| 6,133,220 A | 10/2000 | Baeck et al. | |
| 6,267,952 B1 | 7/2001 | Mandeville, III et al. | |
| 6,326,182 B1 | 12/2001 | Webster et al. | |
| 6,337,187 B1 | 1/2002 | Kapeller-Libermann | |

FOREIGN PATENT DOCUMENTS

WO  WO 99/48471 A1  9/1999

OTHER PUBLICATIONS

Muzny et al., Accession No. AC107039, Database GenBank (National Library of Medicine, Bethesda, MD), Jan. 2002.

Gupta, A.K., et al., "Molecular Differentialtion of Seven *Malassezia* Species", Journal of Clinical Microbiology, pp. 1869–1875 (May 2000).

Mancianti, F., et al., "Extracellular Enzymatic Activity of *Malassezia* spp. Isolates", Mycopathologia, vol. 149, NO. 3, pp. 131–135 (2001).

L.I. Plotkin et al., Characterization of the Lipase Activity of *Malassezia* furfur. 1996 ISHAM, Journal of Medical & Veterinary Mycology 1996. 34, 43–48.

*Primary Examiner*—Elizabeth Slobodyansky
(74) *Attorney, Agent, or Firm*—Brent M. Pebbles; Laura L. Frieko

(57) ABSTRACT

Disclosed is a novel polypeptide having an amino acid sequence substantially as shown in SEQ ID NO:2, or substantially similar to the amino acid sequence encoded by the DNA insert contained in ATCC Deposit No. PTA-4086. Also disclosed is an isolated polynucleotide substantially as shown in SEQ ID NO:1, or substantially similar to a nucleotide sequence contained in a plasmid having all of the identifying characteristics of ATCC Deposit No PTA-4086, encoding the polypeptide. Further disclosed is an expression system comprising the above polynucleotide.

2 Claims, No Drawings

SEQUENCE LISTING

<160> NUMBER OF SEQ ID NOS: 2

<210> SEQ ID NO 1
<211> LENGTH: 918
<212> TYPE: DNA
<213> ORGANISM: malassezia globosa
<220> FEATURE:
<221> NAME/KEY: CDS
<222> LOCATION: (76)..(912)
<223> OTHER INFORMATION:
<220> FEATURE:
<221> NAME/KEY: mat_peptide
<222> LOCATION: (76)..()
<223> OTHER INFORMATION:

<400> SEQUENCE: 1

```
atgctcttca gtcgctttgt tcttcttgcg ttcggttcgg tggccgccgt ctcggccagc      60
agtatttacg cccgt ggc cgt ggt ggt agc tct acc gac cag cca gtg gca     111
              Gly Arg Gly Gly Ser Ser Thr Asp Gln Pro Val Ala
                1               5                  10 aac cct tac aac acc aaa gag att tct ctg gct gcc ggt ctt gtc cag       159
Asn Pro Tyr Asn Thr Lys Glu Ile Ser Leu Ala Ala Gly Leu Val Gln
         15                  20                  25 caa act tac tgt gac agc acg gaa aat ggt ctg aag att ggc gac agc       207
Gln Thr Tyr Cys Asp Ser Thr Glu Asn Gly Leu Lys Ile Gly Asp Ser
 30                  35                  40 gag ctc ctt tac acc atg gga gag ggt tac gct cgc cag cgt gtc aac       255
Glu Leu Leu Tyr Thr Met Gly Glu Gly Tyr Ala Arg Gln Arg Val Asn
 45                  50                  55                  60 atc tat cac tcg cct agc ctt ggt att gct gtg gcc atc gag ggc acg       303
Ile Tyr His Ser Pro Ser Leu Gly Ile Ala Val Ala Ile Glu Gly Thr
                 65                  70                  75 aac ctt ttc tcg ctt aac tcg gac ttg cat gat gcg aag ttc tgg caa       351
Asn Leu Phe Ser Leu Asn Ser Asp Leu His Asp Ala Lys Phe Trp Gln
             80                  85                  90 gaa gac ccg aac gag cgt tac atc cag tac tac ccg aag ggt aca aag       399
Glu Asp Pro Asn Glu Arg Tyr Ile Gln Tyr Tyr Pro Lys Gly Thr Lys
         95                  100                 105 ctt atg cac ggt ttc cag caa gcc tac aat gac ttg atg gat gat atc       447
Leu Met His Gly Phe Gln Gln Ala Tyr Asn Asp Leu Met Asp Asp Ile
110                 115                 120 ttc act gca gtt aag aag tac aag aaa gag aag aat gaa aag cgc gtg       495
Phe Thr Ala Val Lys Lys Tyr Lys Lys Glu Lys Asn Glu Lys Arg Val
125                 130                 135                 140 act gtc att ggc cac tcg ctt ggt gcc gct atg ggt ttg ctt tgc gct       543
Thr Val Ile Gly His Ser Leu Gly Ala Ala Met Gly Leu Leu Cys Ala
                145                 150                 155 atg gac att gag ctg cgt atg gat ggt ggt ctg tac aag acg tac ctg       591
Met Asp Ile Glu Leu Arg Met Asp Gly Gly Leu Tyr Lys Thr Tyr Leu
            160                 165                 170 ttt gga ctt ccc cgt ctt ggt aac cca aca ttt gct tcg ttc gtt gac       639
Phe Gly Leu Pro Arg Leu Gly Asn Pro Thr Phe Ala Ser Phe Val Asp
        175                 180                 185 caa aag att ggc gac aag ttc cac tca att atc aat ggt cgc gac tgg       687
Gln Lys Ile Gly Asp Lys Phe His Ser Ile Ile Asn Gly Arg Asp Trp
    190                 195                 200 gtt cca acg gtg ccg ccg cgc gct ctt ggt tac cag cac cca tct gac       735
Val Pro Thr Val Pro Pro Arg Ala Leu Gly Tyr Gln His Pro Ser Asp
205                 210                 215                 220 tat gtt tgg atc tac cca ggc aac agc acg agc gcg aag ctt tac cct       783
```

```
Tyr Val Trp Ile Tyr Pro Gly Asn Ser Thr Ser Ala Lys Leu Tyr Pro
            225                 230                 235 ggc caa gag aat gtc cac ggt atc ctc act gtt gct cgc gag ttc aac      831
Gly Gln Glu Asn Val His Gly Ile Leu Thr Val Ala Arg Glu Phe Asn
            240                 245                 250 ttt gac gac cac caa ggt atc tac ttc cac acc cag atc ggt gct gtt      879
Phe Asp Asp His Gln Gly Ile Tyr Phe His Thr Gln Ile Gly Ala Val
            255                 260                 265 atg ggt gag tgc cca gct cag gtt ggt gct cat taatga                   918
Met Gly Glu Cys Pro Ala Gln Val Gly Ala His
            270                 275
```

<210> SEQ ID NO 2
<211> LENGTH: 279
<212> TYPE: PRT
<213> ORGANISM: malassezia globosa

<400> SEQUENCE: 2

```
Gly Arg Gly Gly Ser Ser Thr Asp Gln Pro Val Ala Asn Pro Tyr Asn
1               5                   10                  15

Thr Lys Glu Ile Ser Leu Ala Ala Gly Leu Val Gln Gln Thr Tyr Cys
            20                  25                  30

Asp Ser Thr Glu Asn Gly Leu Lys Ile Gly Asp Ser Glu Leu Leu Tyr
        35                  40                  45

Thr Met Gly Glu Gly Tyr Ala Arg Gln Arg Val Asn Ile Tyr His Ser
    50                  55                  60

Pro Ser Leu Gly Ile Ala Val Ala Ile Glu Gly Thr Asn Leu Phe Ser
65                  70                  75                  80

Leu Asn Ser Asp Leu His Asp Ala Lys Phe Trp Gln Glu Asp Pro Asn
                85                  90                  95

Glu Arg Tyr Ile Gln Tyr Tyr Pro Lys Gly Thr Lys Leu Met His Gly
            100                 105                 110

Phe Gln Gln Ala Tyr Asn Asp Leu Met Asp Asp Ile Phe Thr Ala Val
        115                 120                 125

Lys Lys Tyr Lys Lys Glu Lys Asn Glu Lys Arg Val Thr Val Ile Gly
    130                 135                 140

His Ser Leu Gly Ala Ala Met Gly Leu Leu Cys Ala Met Asp Ile Glu
145                 150                 155                 160

Leu Arg Met Asp Gly Gly Leu Tyr Lys Thr Tyr Leu Phe Gly Leu Pro
                165                 170                 175

Arg Leu Gly Asn Pro Thr Phe Ala Ser Phe Val Asp Gln Lys Ile Gly
            180                 185                 190

Asp Lys Phe His Ser Ile Ile Asn Gly Arg Asp Trp Val Pro Thr Val
        195                 200                 205

Pro Pro Arg Ala Leu Gly Tyr Gln His Pro Ser Asp Tyr Val Trp Ile
    210                 215                 220

Tyr Pro Gly Asn Ser Thr Ser Ala Lys Leu Tyr Pro Gly Gln Glu Asn
225                 230                 235                 240

Val His Gly Ile Leu Thr Val Ala Arg Glu Phe Asn Phe Asp Asp His
                245                 250                 255

Gln Gly Ile Tyr Phe His Thr Gln Ile Gly Ala Val Met Gly Glu Cys
            260                 265                 270

Pro Ala Gln Val Gly Ala His
        275
```

FUNGAL LIPASE

CROSS REFERENCE TO RELATED APPLICATION

The application claims the benefit of U.S. Provisional application Ser. No. 60/357,801 (Case 8871 P), filed on Feb. 19, 2002, US Provisional application Ser. No. 60/358,198 (Case 8871P2), filed on Feb. 20, 2002, and US Provisional application Ser. No. 60/361,003 (Case 8871P3), filed on Mar. 1, 2002 in the names of Dawson et al.

FIELD

The present invention relates to an isolated fungal lipase. The invention also relates to a polynucleotide encoding the fungal lipase. The invention further relates to methods for producing the lipase and polynucleotide encoding the lipase. The invention further relates to methods of using the lipase to screen for inhibitors of the lipase.

BACKGROUND

Dandruff is conservatively estimated to be suffered by greater than 50% of the population. This common condition is harmless, but irritating, and is characterized by the shedding of dead skin from the scalp. The usual cause of the condition is seborrheic dermatitis, an itchy, scaly rash on the scalp. The negative effects of dandruff range from aesthetic in the form of white flakes in the hair and/or on the collar and shoulders an afflicted individual's clothing, to physical discomfort in the form of an itching scalp.

Over the years, several actives have been developed for treating dandruff. These anti-dandruff actives include zinc pyrithione, coal tar, and selenium sulfide. While these actives range in efficacy, there is a continued need for more efficacious actives, and/or similarly efficacious but less expensive actives, and/or effective actives that provide greater formulation flexibility. To that end, there is a need for new tools to identify such new anti-dandruff actives.

SUMMARY

The present invention is directed to an isolated fungal lipase, the polypeptide comprising the amino acid sequence substantially as shown in SEQ ID NO:2; or substantially similar to the amino acid sequence encoded by the DNA insert contained in ATCC Deposit No. PTA-4086.

The invention further relates to an isolated polynucleotide encoding the fungal lipase, the polynucleotide comprising the nucleotide sequence substantially as shown in SEQ ID NO:1; substantially similar to the polynucleotide insert contained in ATCC Deposit No. PTA-4086; encoding an amino acid sequence substantially similar to the amino acid sequence encoded by the DNA insert contained in ATCC Deposit No. PTA-4086; or complementary to any of the foregoing nucleotide sequences.

The invention further relates to a nucleic acid vector comprising one of the above nucleic acid sequences.

The invention further relates to host cell comprising the foregoing vector.

The invention further relates to a method for producing a polypeptide comprising the amino acid sequence substantially as shown in SEQ ID NO:2, or substantially similar to the amino acid sequence encoded by the DNA insert contained in ATCC Deposit No. PTA-4086; the method comprising introducing a nucleotide sequence encoding the polypeptide into a host cell, and culturing the host cell under conditions in which the polypeptide is expressed from the nucleic acid.

The invention further relates to a method for identifying lipase inhibitors comprising contacting a lipase polypeptide with a candidate inhibitor material in the presence of a lipid for a period of time, and subsequently measuring for lipid hydrolysis; wherein the lipase polypeptide has the amino acid sequence substantially as shown in SEQ ID NO:2, or substantially similar to the amino acid sequence encoded by the DNA insert contained in ATCC Deposit No. PTA-4086.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

Applicants have answered the need for a means for identifying new actives for treating dandruff. Specifically, Applicants have identified a polypeptide, and polynucleotide encoding the polypeptide, which is believed to be required for the growth of a fungus associated with dandruff.

The fungus genus *Malassezia* is associated with several human skin diseases and conditions including pityriasis versicolor, folliculitis, seborrhoeic dermatitis, atopic dermatitis, and dandruff (Faergemann, J. *Pityrosporum Yeasts* —What's New?, Mycoses (1997) 40: 29–32). *Malassezia*, formerly known as *Pityrosporum*, is a newly described genus. Within the genus, there are seven described species: *pachydermatis, furfur, globosa, sympodialis, restricta, sloofiae,* and *obtusa* (Gueho, E., T. Boekhout, H. R. Ashbee, J. Guillot, A. van Belkum, and J. Faergemann, The role of *Malassezia* species in the ecology of human skin and as pathogens, Medical Mycology (1998) 36 Suppl. I: 220–229). Recently these species have been distinguished by using genomic differences within the ribosomal DNA region (Gupta, A. K., Y. Kohli, and R. C. Summerbell, Molecular differentiation of seven *Malassezia* species, J. Clinical Microbiology (2000) 38: 1869–1875) and by growth in the presence of different lipid emulsifying agents (Mayser, P., P. Haze, C. Papavassilis, M. Pickel, K. Gruender, and E. Gueho, Differentiation of *Malassezia* species: selectivity of Cremophor EL, castor oil and ricinoleic acid for *M. furfur,* British J. of Dermatology (1997) 137: 208–213). With the exception of *M. pachydermatis,* these species are found on human skin.

Six of the seven *Malasseazia* species require lipid for growth, and the seventh species, *M. pachydermatis,* is lipophilic (Guillot, J., and R. Bond, *Malassezia pachydermatis:* a review, Medical Mycology (1999) 37: 295–306). In laboratory culture, the lipid requirement can be met by olive oil (Mayser, P., M. Pickel, P. Haze, F. Erdmann, C. Papavassilis, and R. Schmidt, Different Utilization of Neutral Lipids by *Malassezia furfur* and *Malassezia sympodialis,* Medical Mycology (1998) 36: 7–14). This raises the question whether lipid is also required for growth of these organisms when they are present on human skin. If so, then disruption of lipid metabolism would reduce the number of *Malassezia* on human skin, resulting in a reduction of severity of the human skin maladies associated with *Malassezia,* including dandruff.

A lipase has been described from *M. furfur* (Ran, Y., T. Yoshiike, and H. Ogawa, Lipase of *Malassezia furfur* some properties and their relationship to cell growth, J. Medical and Veterinary Mycology (1993) 31:77–85; Plotkin, L. I., L. Squiquera, l. Mathov, R. Galimberti, and J. Leoni, Characterization of the lipase activity of *Malassezia furfur*, J. Medical and Veterinary Mycology (1996) 34: 43–48; Muhsin, T. M., A. H. Aubaid, and A. H. Al-Duboon, Extracellular enzyme activities of dermatophytes and yeast isolates on solid media, Mycoses (1997) 40: 465–469). However, lipases have not been described for other species of *Malassezia*.

There have been very few genes isolated from *Malassezia*. There are examples of cloned chitin synthase genes (Kano, R. T. Aizawa, Y. Nakamura, S. Watanabe, and A. Hasegawa, Chitin synthase 2 gene sequence of *Malassezia* species, Microbiol. Immunol. (1999) 43: 813–815) and antigen-coding genes and cDNA's (Lindborg, M., C. G. M. Magnusson, A. Zargari, M. Schmidt, A. Scheynius, R. Crameri, and P. Whitley, Selective cloning of allergens from the skin colonizing yeast *Malassezia furfur* by phage display technology, J. Investigative Dermatology (1999) 113: 156–161; Yasueda, H. T. Hashida-Okado, A. Saito, K. Uchida, M. Kuroda, Y. Onishi, K. Takahashi, H. Yamaguchi, K. Takesako, and K. Akiyama, Identification and cloning of two novel allergens from the lipophilic yeast, *Malassezia furfur*, Biochemical and Biophysical Research Communications (1998) 248: 240–244; Schmidt, M., A. Zargari, P. Holt, L. Lindbom, U. Hellman, P. Whitley, I. van der Ploeg, B. Harfast, and A. Scheynius, The complete cDNA sequence and expression of the first major allergenic protein of *Malassezia furfur*, Mal f 1, Eur. J. Biochem (1997), 246: 181–185; Rasool, O., A. Zargari, J. Almqvist, H. Eshaghi, P. Whitley, and A. Scheynius, Cloning, characterization and expression of complete coding sequences of three IgE binding *Malassezia furfur* allergens, Mal f 7, Mal f 8 and Mal f 9, Eur. J. Biochem (2000) 267: 4355–4361; Crameri, R. R. Kodzius, Z. Konthur, H. Lehrach, K. Blaser, and G. Walter, Tapping allergen repertoires by advanced cloning technologies, Int Arch Allergy Immunol (2001) 124: 43–47), one of which has similarity to a mitochondrial malate dehyrogenase gene (Onishi, Y. M. Kuroda, H. Yasueda, A. Saito, E. Sono-Koyama, S. Tunasawa, T. Hashida-Okado, T. Yagihara, K. Uchida, H. Yamaguchi, K. Akiyama, I. Kato, and K. Takesako, Two-dimensional electrophoresis of *Malassezia* allergens for atopic dermatitis and isolation of Mal f 4 homologs with mitochondrial malate dehydrogenase, Eur. J. Biochmistry (1999) 261: 148–154). However, no one has reported the isolation of a polynucleotide sequence encoding a lipase from any *Malassezia* species.

All documents cited herein are, in relevant part, incorporated herein by reference; the citation of any document is not to be construed as an admission that it is prior art with respect to the present invention.

All percentages are by weight of total composition unless specifically stated otherwise.

All ratios are weight ratios unless specifically stated otherwise.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "isolated", in reference to the polypeptide embodiment of the present invention or polynucleotide embodiment encoding the polypeptide, means that the polypeptide or polynucleotide exists apart from the complex cellular milieu in which it naturally occurs, and the polypeptide is expressible from the polynucleotide in a cell that does not naturally express it when operably linked to the appropriate regulatory sequences. Specifically, when applied to polynucleotides (e.g., DNA), "isolated" indicates the DNA is substantially isolated with respect to (i.e., exists substantially apart from) the complex cellular milieu in which it naturally occurs, or is simply present in a different nucleic acids context from that in which it occurs in nature (for example, when cloned or in the form of a restriction fragment). Thus, the polynucleotide or polypeptide of the invention may be present in a wide variety of vectors, and/or in any of a wide variety of host cells (or other milieu, such as buffers, viruses or cellular extracts), and/or in any variety of compositions; yet still be isolated in the sense used herein in that such vector, host cell or composition is not part of the natural environment of the polynucleotide or polypeptide.

Herein, "substantially as shown" or "substantially similar", with respect to a polypeptide, means the same or sufficiently similar in structure or amino acid sequence to serve its principal function; or with respect to a polynucleotide, means the same or sufficiently similar in structure or nucleotide sequence to encode the desired polypeptide or gene product. In other words, a particular subject sequence (amino acid or nucleotide sequence), for example altered by mutagenesis, varies from a reference sequence by one or more substitutions, deletions or additions, the net effect of which is to retain biological activity of the reference polypeptide. Alternatively, nucleotide sequences and analogs are "substantially similar" to the specific nucleotide sequence disclosed herein if the nucleotide sequences, as a result of degeneracy in the genetic code, encode an amino acid sequence substantially similar to the reference amino acid sequence. In addition, "substantially similar" means a polypeptide that will react with antibodies generated against the polypeptide or peptides derived from the polypeptide of the invention.

Herein, "sequence identity" is determined by aligning two subject polypeptide (amino acid) or polynucleotide sequences for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 50%, more preferably at least 60%, and even more preferably at least 70%, 80%, or 90% of the length of the reference sequence (i.e., 100% equals the entire coding sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, disregarding the number of gaps, and the length of each gap, which need to be introduced for optimal alignment of the two sequences.

The biological deposits referred to herein will be maintained under the terms of the Budapest Treaty on the International Recognition of the Deposit of Microorganisms for purposes of Patent Procedure. Consequently, the deposits are available as required by the patent laws in countries wherein counterparts of this patent application, or its progeny, are filed. However, Applicants' granting of such permission to the depository to distribute samples of the deposit does not constitute an express or implied license to practice the invention claimed in any patent issuing on the subject patent application or any other patent. The deposit is provided merely as a convenience to those skilled in the art, and is not an admission that the deposited material is essential to the practice of the present invention. The nucleotide sequence of the polynucleotide contained in the deposited material, as well as the amino acid sequence of the polypeptide encoded thereby, are incorporated herein by reference in the event of any conflict with any description of sequences herein. It is noted that one of ordinary skill in the art reproducing Applicants' work from the written disclosure can discover any such sequencing conflicts using routine skill.

A. Polypeptide

One embodiment of the present invention relates to an isolated polypeptide having an amino acid sequence substantially as shown in SEQ ID NO:2; or substantially similar to the amino acid sequence encoded by a nucleotide sequence contained in a plasmid having all the identifying characteristics of Deposit No. PTA-4086 (hereinafter collectively referred to as the "lipase polypeptide").

Herein "polypeptide" refers to a polymer made up of amino acids linked together to form peptide bonds, preferably forming a preproprotein, proprotein, protein or fragment thereof. Herein "preproprotein" refers to a polypeptide consisting of a signal sequence, a pro region, and a mature region; and "proprotein" refers to a polypeptide consisting of a pro region and a mature region. Depending upon the host employed in a recombinant production procedure, the lipase polypeptide may be glycosylated or may be non-glycosylated. The lipase polypeptide may also include an initial methionine amino acid residue.

The lipase polypeptide may be obtained by purification from a naturally occurring source, expression from a recombinantly engineered source, chemical synthesis, or a combination thereof.

In one embodiment, the lipase polypeptide is an amini acid sequence which has at least about 60% sequence identity (i.e., homology) to the amino acid sequence as shown in SEQ ID NO:2, or as contained in a plasmid having all of the identifying characteristics of ATCC Deposit No. PTA-4086; more preferably at least about 80%; more preferably at least about 90%, more preferably at least about 95%; more preferably at least about 98%. Preferably sequences having such sequence identity are capable of providing lipase activity.

B. Polynucleotide

Another embodiment of the present invention relates to an isolated polynucleotide comprising a nucleotide sequence substantially as shown in SEQ ID NO:1, substantially similar to a nucleotide sequence contained in a plasmid having all of the identifying characteristics of ATCC Deposit No. PTA-4086, or which encodes the lipase polypeptide (hereinafter collectively referred to as the "lipase polynucleotide").

Herein, "polynucleotide" refers to a polymer of DNA or RNA which can be single-or double-stranded, optionally containing synthetic, non-natural or altered nucleotide bases capable of incorporation into DNA or RNA polymers. The polynucleotide may be in the form of a separate fragment or as a component of a larger nucleotide sequence construct, which has been derived from a nucleotide sequence isolated at least once in a quantity or concentration enabling identification, manipulation, and recovery of the sequence and its component nucleotide sequences by standard biochemical methods, for example, using a cloning vector. Genomic DNA containing the relevant sequences could also be used. Sequences of non-translated nucleotides may be present 5' or 3' from the open reading frame, where the same do not interfere with manipulation or expression of the coding regions. Polynucleotides encoding the polypeptide provided by this invention can be assembled from DNA fragments and short oligonucleotide linkers, or from a series of oligonucleotides, to provide a synthetic gene which is capable of being expressed in a recombinant transcriptional unit.

The lipase polynucleotide of the present invention embraces nucleotide sequences having any sequence so long as it encodes the lipase polypeptide. As a result of degeneracy in the genetic code, any particular amino acid sequence may be encoded by many different nucleotide sequences. The skilled artisan will appreciate that the degeneracy of the genetic code allows for differing nucleotide sequences to provide the same polypeptide. In certain cases preparing a nucleotide sequence, which encodes for the same peptide but differs from the native nucleotide sequence, provides various advantages, including: ease of sequencing or synthesis, increased expression of the peptide, and/or preference of certain heterologous hosts for certain codons over others. These practical considerations are widely known and provide embodiments that may be advantageous to the user of the invention. Thus it is clearly contemplated that the native nucleotide sequence, or nucleotide sequence listed in the Sequence Listing, or incorporated by reference are not the only embodiments or nucleotide sequences envisioned by this invention.

The lipase polynucleotide can be in the form of RNA, such as mRNA, or in the form of DNA, including cDNA and genomic DNA obtained by purification from a naturally-occurring source, cloning, produced by chemical synthetic techniques, or by a combination thereof. The nucleic acid, especially DNA, can be double-stranded or single-stranded. Single-stranded nucleic acid can be the coding strand (sense strand) or the non-coding strand (anti-sense strand).

In one embodiment, the lipase polynucleotide is a nucleotide sequence which has at least about 60% sequence identity (i.e., homology) to the nucleotide sequence as shown in SEQ ID NO:1, or as contained in a plasmid having all of the identifying characteristics of ATCC Deposit No. PTA-4086; more preferably at least about 80%; more preferably at least about 90%, more preferably at least about 95%; more preferably at least about 98%. Preferably sequences having such sequence identity are capable of encoding a lipase polypeptide.

C. Expression System

Another aspect of the present invention relates to an expression system comprising the lipase polynucleotide. Such expression systems include recombinant expression vectors comprising the lipase polynucleotide, as well as hosts which have been genetically engineered with such recombinant expression vectors ("recombinant host").

1. Vector

Herein, "recombinant expression vector" refers to a DNA construct used to express a polynucleotide which encodes a desired polypeptide (for example, the lipase polypeptide) and which includes a transcriptional subunit comprising an assembly of 1) genetic elements having a regulatory role in gene expression, for example, promoters and enhancers, 2) a structural or coding sequence which is transcribed into mRNA and translated into protein, and 3) appropriate transcription and translation initiation and termination sequences. Using methodology well known in the art, recombinant expression vectors of the present invention can be constructed. The nature of the vector is not critical to the invention, and any vector may be used, including plasmid, virus, bacteriophage, and transposon. Possible vectors for use in the present invention include, but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. Additional useful vectors include, but are not limited to: for mammalian cells, pcDNA-1 (Invitrogen, San Diego, Calif.) and pSV-SPORT 1 (Gibco-BRL, Gaithersburg, Md.); for insect cells, pBlueBac lll or pBlueBacHis baculovirus vectors (Invitrogen, San Diego, Calif.); and for bacterial cells, pET-3 (Novagen, Madison, Wis.). Any other vector may be used as well, as long as it is replicable and viable in the host. The lipase polynucleotide can be present in the vector operably linked to regulatory elements.

The lipase polynucleotide may be inserted into the vector by a variety of procedures. In general, the polynucleotide is inserted into an appropriate restriction endonuclease site(s) by procedures known in the art. Such procedures and others are deemed within the scope of those skilled in the art.

The vector may preferably comprise an expression element or elements operably linked to the lipase polynucleotide to provide for expression thereof at suitable levels. Any of a wide variety of expression elements may be used. The expression element or elements may, for example, be selected from promoters, enhancers, ribosome binding sites, operators and activating sequences. Such expression elements may be regulatable, for example, inducible (via the addition of an inducer). Representative examples of useful promoters include, but are not limited to: LTR (long terminal repeat from a retrovirus) or SV40 promoter, the *E. coli* lac or trp promoter, the phage Lambda $P_L$ promoter, and other promoters known to control expression of genes in prokaryotic or eukaryotic cells or their viruses. The expression vector preferably also contains a ribosome binding site for translation initiation and a transcription terminator. The expression vector may also include appropriate sequences for amplifying expression.

In a preferred embodiment, the expression vector further contains one or more selectable marker genes to provide a phenotypic trait for selection of transformed host cells such as dihydrofolate reductase or neomycin resistance for eukaryotic cell cultures, or such as tetracycline or ampicillin resistance for prokaryotic cell cultures.

Useful expression vectors for bacterial use are constructed by inserting the lipase polynucleotide with suitable translation initiation and termination signals in operable reading frame with a functional promoter. The vector will preferably contain one or more phenotypic selectable markers and an origin of replication to ensure maintenance of the vector and to, if desirable, provide amplification within the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and pGEM1 (Promega Biotec, Madison, Wis., U.S.A.). These pBR322 "backbone" sections are combined with an appropriate promoter and the LIPASE polypeptide to be expressed. Other suitable bacterial vectors include: pQE70, pQE60, and pQE-9 (Qiagen); pbs, pD10, phagescript, psiX174, pBluescript SK, pbsks, pNH8A, pNH16a, pNH18A, and pNH47A (Stratagene); and ptrc99a, pKK223-3, pKK233-3, pDR540, and pRIT5 (Pharmacia).

Useful expression vectors for use with yeast can comprise a yeast replication origin or fragments of DNA which are required for integration into the host's chromosomal DNA, a selectable marker, a suitable promoter and enhancer, and also any necessary ribosome binding sites, a polyadenilation site, transcriptional termination sequences and 5' flanking nontranscribed sequences. Suitable yeast expression vectors include, but are not limited to, pPIC3, pPIC3K, pPIC3.5K, pPIC9, pPIC9K, pAO815, pHIL-D2, pHIL-S1, pPICZaA, pPICZaB, and pPICZaC (Invitrogen) preferably for *Pichia pastoris;* pYES2 (Invitrogen), and the pRS series vectors (STRATAGENE) preferably for *Saccharomyces cerevisiae*.

Mammalian expression vectors will preferably comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the necessary nontranscribed genetic elements.

Suitable mammalian vectors, by way of non-limiting example, include: pWLNEO, pOG44, pXT1, pSG (Stratagene); pSVK3, pBPV, pMSG, pSVL (Pharmacia).

2. Host

The recombinant expression vector containing the lipase polynucleotide as well as an appropriate promoter or control sequence, may be employed to transform an appropriate host to permit the recombinant host to express the lipase polypeptide.

Recombinant hosts may include bacterial, fungal, insect, plant or mammalian cells which have been transformed with a recombinant expression vector of the present invention. Recombinant hosts may also include entire plants, insects or non-human mammals which have been transformed with the recombinant expression vector. Representative examples of appropriate hosts for in vitro production include: bacterial cells such as *E. coli, Salmonella typhimurium, Bacillus subtilis*, and various species within the general *Pseudomonas, Streptomyces*, and *Staphylococcus*, although others may also be employed as a matter of choice; yeast or fungal cells such as *Pichia pastoris, Candida boidinii*, and *Saccharamyces cervisiae*; insect cells such as *Drosophila* and Sf9; animal cells such as the COS-7 lines of monkey kidney fibroblasts (described by Gluzman, CELL, 23:175 (1981)), C127 (mouse), 3T3 (mouse), CHO (hamster) and BHK (hamster); human cells such as HeLa. Alternatively, recombinant hosts for in, vivo production in non-human mammals include, but are not limited to, cows, goats, guinea pigs, hamsters, mice, pigs, rabbits and sheep; insects including silk worm larvae; and plants. The selection of an appropriate host is deemed to be within the scope of those skilled in the art from the teachings herein.

Herein, "transformation" means introducing DNA into a cell or an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N., PROC. NATL. ACAD. SCI. (USA), 69:2110 (1972); Mandel et al., J. MOL. BIOL., 53:154 (1970); and Lilgestrom et al., GENE, 40:241–246 (1985), is generally used for prokaryotes or other cells that contain substantial cell-wall barriers. For mammalian cells without such cell walls, the calcium phosphate precipitation method of Graham and van der Eb, VIROLOGY, 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, et al., J. BACT., 130:946 (1977) and Hsiao, et al, PROC. NATL. ACAD. SCI. (USA), 76:3829 (1979). Alternatively, introduction of the expression vector into the host can be effected by calcium phosphate transfection, DEAE-Dextran mediated transfection, or electroporation as set forth in BASIC METHODS IN MOLECULAR BIOLOGY (D. L. Davis and I. M. Battey, (1986)). However, other methods for introducing DNA into cells such as by nuclear injection or by protoplast fusion may also be used.

D. Recombinantly Producing Lipase Polypeptide

One aspect of the invention relates to a process for producing an isolated lipase polypeptide via recombinant technology. The process comprises inserting the lipase polynucleotide into a suitable recombinant expression vector (as described above), and then transforming a suitable host with this recombinant expression vector (as described above). The transformed host is subsequently used to express the lipase polypeptide, followed by purification of the resulting lipase polypeptide from the host.

In one embodiment, the recombinant lipase polypeptide is produced so that the lipase polypeptide is secreted from the host cell (Mileto, D., S. Brocaa, M. Lotti, M. Takagi, C. Alquati, and L. Alberghina, Characterization of the *Candida rugosa* Lipase System and Overexpression of the Lip1 Isoenzyme in a Non-conventional Yeast, Chemistry of Physics of Lipids (1998) 93: 47–55). This may be done by fusing a signal sequence from a different secreted protein with the lipase polypeptide (Qasim, M. A., P. J Ganz, C. W. Saunders, K. S. Bateman, M. N. G. James, and M. Laskowski, Jr., Interscaffolding Additivity. Association of $P_1$ Variants of Eglin c and of Turkey Ovomucoid Third Domain with Serine Proteinases, Biochemistry (1997) 36: 1598–1607). Alternatively, the lipase polypeptide may be produced within the host cell. In one embodiment of this procedure, the lipase polypeptide is produced as part of a fusion protein (Tang, S., K. Sun, G. Sun, T. Chang, and G. Lee, Recombinant Expression of the *Candida rugosa* lip4 Lipase in *Escherichia coli*, Protein Expression and Purification (2000) 20: 308–313).

In a preferred embodiment, the method comprises culturing a yeast host cell which has been transformed with a recombinant expression vector comprising the lipase polynucleotide. The cultured yeast host cell is subsequently used to produce the lipase polypeptide, followed by purification of the resulting lipase polypeptide from the cultured medium. An embodiment of this procedure includes fusing the lipase polynucleotide with the gene for the *Saccharomyces cerevisae* α-factor such that the α-factor signal sequence (Kurjan, J., and 1. Herskowitz, Structure of a Yeast Pheromone Gene (MFα): A Putative α-Factor Precursor Contains Four Tandem Copies of Mature α-Factor, Cell (1982) 30: 933–943) directs the secretion of the lipase polypeptide.

Following transformation of a suitable host strain and growth of the host strain to an appropriate cell density, the selected promoter is induced by appropriate means (e.g., temperature shift or chemical induction) and cells are cultured for an additional period.

In an alternative alternative embodiment to modifying host cells to secrete lipase polypeptide into the culture medium, the hosts could be modified to produce lipase polypeptide which accumulates within the cells. Such cells are typically harvested by centrifugation, disrupted by physical or chemical means, and the resulting crude extract retained for further purification.

Microbial cells employed in expression of the lipase polypeptide can be disrupted by any convenient method, including freeze-thaw cycling, sonication, mechanical disruption, or use of cell lysing agents; such methods are well known to those skilled in the art.

The lipase polypeptide can be recovered and purified from the recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

E. Chemically Synthesizing Lipase Polypeptide

The lipase polypeptide may be generated through chemical synthesis, using methods well known to those skilled in the art for chemically synthesizing proteins (see, e.g., Wilce, J. A., S. G. Love, S. J. Richardson, P. F. Alewood, and D. J. Craik, Synthesis of an analog of the thyroid hormone-binding protein transthyretin via regioselective chemical ligation).

F. Chemically Synthesizing Lipase Polvnucleotide

The lipase polynucleotide may be generated through chemical synthesis using methods well known to those skilled in the art (see, e.g., Traub, P. C., C. Schmidt-Dannert, J. Schmitt, and R. D. Schmid, Gene Synthesis, Expression in *E. coli* and in vitro refolding of *Pseudomonas* sp. KWI 56 and *Chromobacterium viscosum* lipases and their chaperones, Applied Microbiology and Biotechnology (2001) 55: 198–204.) Such an approach allows the optimization of the synthetic gene for host-specific conditions, such as codon usage.

G. Isolating Other Lipase Genes

The lipase polynucleotide can be used to isolate other lipase genes based on similarities of polynucleotide sequence. For example, the lipase polynucleotide may be substituted for the *Candida albicans* lipase gene in the Southern blot hybridization assay set forth in B. Hube, Stehr, F., Bossenz, M., Mazur, A., Kretschmar, M., and W. Schafer, Secreted Lipases of *Candida albicans:* Cloning, Characterisation and Expression Analysis of a New Gene Family with at least Ten Members, Arch Microbiol (2000) 174:362–74, to identify other lipase genes.

H. Method of Screening for Lipase Inhibitors

The present invention further relates to a method of screening for inhibitors of the lipase polypeptide, comprising contacting the lipase polypeptide with a candidate inhibitor material in the presence of a lipid for a period of time; and subsequently measuring for lipid hydrolysis.

Lipases are enzymes which hydrolyze (break down) lipids (e.g., fats) into glycerol and fatty acids. A variety of means for measuring for lipid hydroysis may be employed in the present method for screening for lipase polypeptide inhibitors. Such methods include measuring for changes in glycerol production following contact with the candidate inhibitor. A decrease in, or no glycerol production indicates that candidate inhibitor material inhibits the lipase polypeptide. Alternatively, the lipid could be coupled to a colormetric compound. If the lipid is hydrolyzed, the system would turn from colorless to, e.g., yellow. No color change would indicate the candidate inhibitor material inhibits the lipase polypeptide. See, e.g., Pablo, G., A. Hammons, S. Bradley, and J. E. Fulton, Characteristics of the Extracellular Lipases from *Corynebacterium acnes* and *Staphylococcus epidermidis*, J. Investigative Dermatology (1974) 63: 231–238. for a description of the use of colorimetric substrates in lipase assays.

I. Other Uses of the Lipase Polypeptide

In addition to being useful for screening for anti-dandruff actives, the lipase polypeptide embodiment of the present invention has other, non-antidandruff uses. For example, it is well known in the laundry detergent art that detergent compositions may advantageously comprise enzyme systems. Such enzyme systems include cellulase, protease, amylase, and lipase. The lipase polypeptide embodiment of the present invention is useful in granular and/or liquid detergent compositions. Examples of granular and liquid detergent composition embodiments in which the lipase polypeptide may be employed include those set forth in U.S. Pat. No. 6,133,220 (granted Oct. 17, 2000 to The Procter & Gamble Company), and U.S. Pat. No. 5,733,473 (granted Mar. 31, 1998 to The Procter & Gamble Company), where the lipase disclosed therein would be substituted with the lipase polypeptide embodiment of the present invention. In an alternative embodiment, the lipase polypeptide would be included in addition to the lipase already employed in such granular or liquid detergent compositions.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

This example shows how to purify the lipase polypeptide from a naturally occurring source.

*M. globosa* cells were cultured in a glass two-liter flask with a cotton plug, shaking at 200 rpm in a New Brunswick Scientific Co. (Edison, N.J.) incubator. We used 500 ml of mDixon medium (per liter water: 36 g malt extract (Difco), 20 g desiccated ox bile (Fluka), 10 ml Tween 40 (Aldrich), 24 g peptone (Difco), 2 ml glycerol (Sigma), 2 ml oleic acid (Baker), pH to 6.0 (with 1 N HCI) with 500 $\mu$g/ml chloramphenicol (IBI). The culture was incubated at 31° for one week after the culture turned opaque, which typically takes five to seven days. The cells were then harvested by spinning at 2900 rpm for ten minutes in a refrigerated Sorvall™ RC3CPLUS centrifuge. The supernatant was removed, and the cell pellet was resuspended in 50 ml of 25 mM Tris HCI pH 8.0. The cells were transferred to 50 ml conical tubes and spun for ten minutes 3750 rpm at room temperature in a Beckman GS6K centrifuge, and the supernatant was removed. The cells were frozen at −80°. The cells were thawed at room temperature and resuspended in eight ml of extraction buffer (25 mM TrisHCl pH 8, 90 mM NaCI, 8 mM KCI, 1 mM $CaCl_2$) per gram of cells.

Lipase was extracted by incubating the cell suspension for two hours at room temperature, mixing by rotation on a Lab Rotator (Lab-Line). The cells were then spun for ten minutes at 3750 rpm in a Beckman GS6K, and the supernatant was collected. The cells were similarly extracted five more times, with the supernatant collected each time. The individual supernatants were assayed for lipase activity (see below), and the active extracts were combined.

To assay for lipase activity, we first prepared a stock solution of substrate, 50 mM p-nitrophenyl oleate, in isopropanol. On the day of the assay, the stock substrate was diluted 40-fold with 25 mM MES pH 5.5. The assay was carried out in a plastic cuvette with one ml of liquid comprising 125 $\mu$l of the 1.25 mM substrate, up to 125 $\mu$l of lipase, and the remaining volume comprised 25 mM MES pH 5.5, 90 mM NaCI, 8 mM KCI, 1 mM $CaCl_2$. The cuvettes are incubated for twenty minutes at room temperature, whereupon 20 $\mu$l of 2 M Tris HCI pH 8 is added to raise the pH. The absorbance at 410 nm is then measured using a Beckman DU® 640 spectrophotometer.

EXAMPLE 2

This example shows how to screen for inhibitors of the lipase polypeptide.

The assay is performed in a deep well 96-well plate (costar® 4412). To each well, 270 $\mu$l of 25 mM MES, pH 5.5, 90 mM NaCI, 8 mM KCI, 1 mM $CaCl_2$ is added. 10 $\mu$l of olive oil (lipid source), diluted three-fold into dimethyl sulfoxide, is then added. A candidate inhibitor (15 $\mu$l) is then added. Then 5 $\mu$l of lipase polypeptide is added. Caps are then used to cover the microtiter plate. The solution is left for one hour at room temperature, with vigorous shaking on a VX-2500 Multi-tube Vortexer (Scientific Products). Following the one-hour period, the microtiter plate is spun briefly in a centrifuge to force the liquid into the bottom of the well.

After spinning, the pH is raised by the addition of 50 $\mu$l of 1 M Tris HCI pH 8.0. A portion (90 $\mu$l) is transferred to a standard microtiter plate (costar® 3596), and 90 $\mu$l of a glycerol detection solution is added. The glycerol detection solution contains: 100 mM Tris HCI pH 7.6, 10 mM $MgCl_2$, 2 mM 4-aminoantipyrine, 3 mM N-ethyl-N-(3-sulfopropyl)-m anisidine, 1 mM adenosine 5'-triphosphate, 20 units/ml peroxidase, 8 units/ml glycerol-3-phosphate oxidase, 0.5 units/ml glycerol kinase. The mixture is rotated on a Lab-Line Lab Rotator for 15 minutes at room temperature. The optical density at 540 nm is measured as an indication of the amount of glycerol produced in the assay. To know the absolute amount of glycerol generated in the assay, one can generate a standard curve with known glycerol concentrations. A comparison is made between the amount of glycerol generated by the lipase polypeptide in the absence of the candidate inhibitor and the amount of glycerol generated by the lipase polypeptide in the presence of the candidate inhibitor. An inhibitor-dependent reduction in glycerol levels of at least two-fold indicates inhibition of the ability of the lipase polypeptide to breakdown lipids.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An isolated polypeptide comprising an amino acid sequence, wherein said amino acid sequence:
   (a) has at least 95% sequence identity to SEQ ID NO:2; or
   (b) has at least 95% sequence identity to the amino acid sequence encoded by the DNA insert contained in ATCC Deposit No. PTA-4086, wherein said polypeptide exhibits lipase activity.

2. A method for identifying lipase inhibitors comprising the step of measuring lipid hydrolysis by contacting the lipase polypeptide of claim 1 with lipid in the presence or absence of a candidate inhibitor.

* * * * *